(12) United States Patent
Hacker

(10) Patent No.: US 9,072,541 B2
(45) Date of Patent: Jul. 7, 2015

(54) SURGICAL SCALPEL HANDLE WITH ILLUMINATOR

(71) Applicant: Steven M. Hacker, Delray Beach, FL (US)

(72) Inventor: Steven M. Hacker, Delray Beach, FL (US)

(*) Notice: Subject to any disclaimer, the term of this patent is extended or adjusted under 35 U.S.C. 154(b) by 83 days.

(21) Appl. No.: 14/061,777

(22) Filed: Oct. 24, 2013

(65) Prior Publication Data

US 2015/0119650 A1 Apr. 30, 2015

(51) Int. Cl.
*A61B 1/06* (2006.01)
*A61B 17/32* (2006.01)
*A61B 17/3211* (2006.01)

(52) U.S. Cl.
CPC ............. *A61B 17/3211* (2013.01); *A61B 1/06* (2013.01)

(58) Field of Classification Search
CPC ............................. A61B 17/3211; A61B 1/06
USPC ........................................................ 600/249
See application file for complete search history.

(56) References Cited

U.S. PATENT DOCUMENTS

| | | | | |
|---|---|---|---|---|
| 4,735,202 A | * | 4/1988 | Williams | 606/167 |
| 5,405,208 A | | 4/1995 | Hsieh | |
| 5,437,657 A | | 8/1995 | Epstein | |
| 5,523,928 A | | 6/1996 | Kim | |
| 5,544,967 A | | 8/1996 | Yao | |
| 5,571,098 A | * | 11/1996 | Domankevitz et al. | 606/15 |
| 5,673,996 A | | 10/1997 | Ducker | |
| 5,700,236 A | * | 12/1997 | Sauer et al. | 600/175 |
| 6,439,734 B1 | | 8/2002 | Lo | |
| 6,483,651 B1 | | 11/2002 | Maurer | |
| 6,733,150 B1 | | 5/2004 | Hanley | |
| 6,830,403 B2 | | 12/2004 | Tsai | |
| 6,895,266 B1 | | 5/2005 | Hollis | |
| 6,999,248 B2 | | 2/2006 | Schuttinger | |
| 7,566,139 B1 | | 7/2009 | Dority | |
| 7,871,375 B2 | | 1/2011 | Talieh | |
| 8,287,534 B2 | | 10/2012 | Balog | |
| 8,414,140 B2 | | 4/2013 | Chang | |
| 8,784,416 B2 | | 7/2014 | Balog | |
| 2003/0171654 A1 | * | 9/2003 | Skaggs | 600/190 |
| 2005/0171408 A1 | * | 8/2005 | Parker | 600/249 |
| 2007/0049794 A1 | * | 3/2007 | Glassenberg et al. | 600/109 |
| 2007/0088374 A1 | * | 4/2007 | Masury et al. | 606/167 |
| 2007/0112257 A1 | * | 5/2007 | Hensler | 600/199 |
| 2010/0125172 A1 | * | 5/2010 | Jayaraj | 600/249 |
| 2012/0149992 A1 | * | 6/2012 | Duggal et al. | 600/245 |

FOREIGN PATENT DOCUMENTS

CN 201394055 Y 2/2010

* cited by examiner

*Primary Examiner* — Kristen Matter

(57) ABSTRACT

A surgical scalpel handle with illuminator allowing the surgeon to use the illumination to light the surgical field while holding the scalpel handle is disclosed. A surgical scalpel handle with an illuminator comprises a scalpel handle that contains, a structural strut, that serves to attach light emitting diode (LED) cartridge with the strut terminating into a bayonet fitting attachment for the blade element; and a light emitting diode (LED) cartridge with a series of light emitting diodes embedded in the cartridge. The LED cartridge is attached to the scalpel handle by sliding the bayonet fitting of the strut through the central axis of the light emitting diode cartridge and then by screwing LED cartridge onto the strut in order to attach to scalpel handle and expose at least a part of the LED cartridge.

21 Claims, 4 Drawing Sheets

SURGICAL SCALPEL HANDLE WITH ILLUMINATOR

FIELD OF INVENTION

The present invention relates to the field of surgical incision, excision and biopsy instruments. In particular, this invention relates to a surgical scalpel handle with an illuminator allowing the surgeon to use the scalpel to illuminate a surgical field immediately adjacent to and in advance of the blade and in the direction of cutting.

BACKGROUND OF THE INVENTION

The present invention relates to the field of surgical incision, excision and biopsy instruments. In particular, this invention relates to a surgical scalpel handle with an illuminator allowing the surgeon to use the scalpel handle to illuminate a surgical field immediately adjacent to and in advance of the blade and in the direction of cutting.

Physicians and surgeons use a scalpel handle to attach to a blade to cut human tissue for a variety of purposes.

Illuminating a surgical field in tight small spaces of the human body and immediately in front of a scalpel blade is challenging for a surgeon.

In the art, many sources of illumination are used. Typical Illumination is provided via an illuminator source attached to surgeon's headset, or held by a surgical assistant, attached to overhead ceiling, or provided using a lamp on wheels in the operating suite and this well known to the art. Prior art devices include clip-on LED lights and incandescent lamps for headwear, glasses with LED light sources with built in with batteries and hand held devices. Such constructions may be seen in U.S. Pat. No. 6,483,651, U.S. Pat. No. 6,733,150, U.S. Pat. No. 6,999,248 B2 and U.S. Pat. No. 7,566,139.

The limitations of the prior art is that none of the existing methods provide illumination immediately adjacent to the scalpel blade and thus the illuminated field is not optimized visually putting at risk unnecessary damage and severing of difficult to visualize neurovascular structures.

Additional limitations are that the sources of illumination frequently require an assistant to hold the source of illumination requiring additional cost to the surgery or hindrance to the surgeon by crowding the surgical field.

Additional limitations to illuminating a surgical field are that most sources require an additional power source that must be attached to either a battery pack or a plug for power. This limitation is also a hindrance to the surgeon in that the surgeon must work around these additional attachments and they are often obtrusive and limiting in portability and mobility. Additional disadvantages of the existing illumination sources are the significant cost and resources necessary to install illumination into outpatient exam rooms.

Accordingly, a methodology which overcomes the shortcomings of prior art is desired.

It is the object of the invention to provide a scalpel handle with an attachable light emitting diode (LED) cartridge containing a series of LED bulbs which can illuminate relatively uniformly the surgical field and can be manufactured relatively readily, and inexpensively.

The main object of the present invention is to provide a surgical scalpel handle that provides illumination immediately adjacent to and in front of a surgical blade.

Another object of the present invention is to provide a surgical scalpel handle that can provide illumination with an attachable light emitting diode cartridge which can illuminate uniformly the immediately adjacent surgical field without shadowing effects from the scalpel blade.

Another object of the present invention is to provide a surgical scalpel handle that can provide illumination using the handle as a source of illumination and removing the need for additional personnel to hold a separate lamp or require additional lamps in the exam room.

Another object of the present invention is to provide a surgical scalpel handle that can provide illumination using a dry battery and avoid the need for power cords that may restrict the movement of the surgeon or staff around the surgical field.

Another object of the present invention is to provide a surgical scalpel handle that can provide illumination that can be manufactured relatively easily and inexpensively.

Another object of the present invention is to provide a reusable non-disposable surgical scalpel handle that can provide illumination with a disposable attachable light emitting cartridge that can be replaced with a new disposable attachable light emitting cartridge.

Another object of the present invention is to provide a disposable surgical scalpel handle that can provide illumination with a disposable attachable light emitting cartridge that can be disposed in the attached condition in their entirety after surgery.

BRIEF SUMMARY OF THE INVENTION

It is the object of the invention to provide a scalpel handle with an attachable light emitting diode (LED) cartridge containing a series of LED bulbs which can illuminate relatively uniformly the surgical field immediately adjacent to and in front of a surgical blade without shadow from the blade and can be manufactured relatively readily, and inexpensively.

BRIEF DESCRIPTION OF THE DRAWINGS

The various features of the present invention and the manner of attaining them will be described in greater detail with reference to the following description, claims, drawings, wherein reference numerals are reused, where appropriate to indicate a correspondence between the referenced items, and wherein the preferred embodiments of the invention will herein after be described in conjunction with appended drawings to illustrate and not to limit the invention wherein like designations denote like elements and in which:

DETAILED DESCRIPTION OF THE PREFERRED EMBODIMENT

Figure 1:
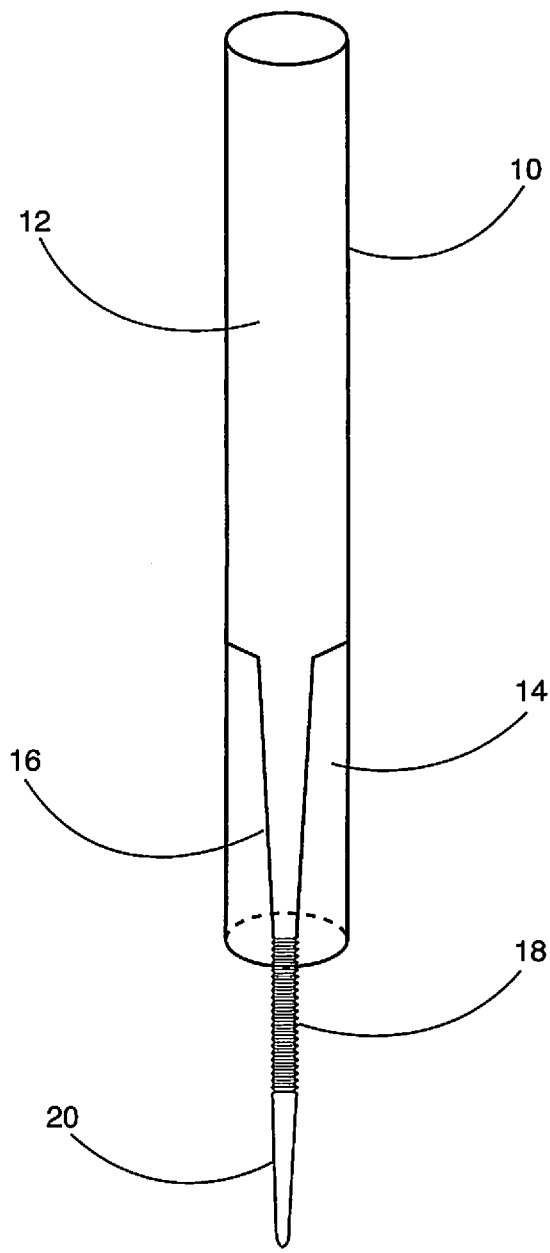
FIG. 1 is a perspective view of a scalpel handle with bayonet fitting and support strut in accordance with the present invention.

FIG. 1 shows a handle defining a barrel 10, a rear portion 12 of the barrel 10 that is solid and a front portion 14 that is hollow, a stabilizing strut support 16 with a rear portion contained along the central axis of the barrel 10 in the front hollow end 14 of the barrel 10 and attached to the rear solid portion 12 of the barrel 10. The strut support 16 has a front exposed portion with threads 18 and is tapered into a bayonet fitting 20 protruding through the front end opening of barrel 10. The diameter of strut support 16 and the front exposed portion with threads 18 is greater than the diameter of the bayonet fitting 20.

Figure 2:
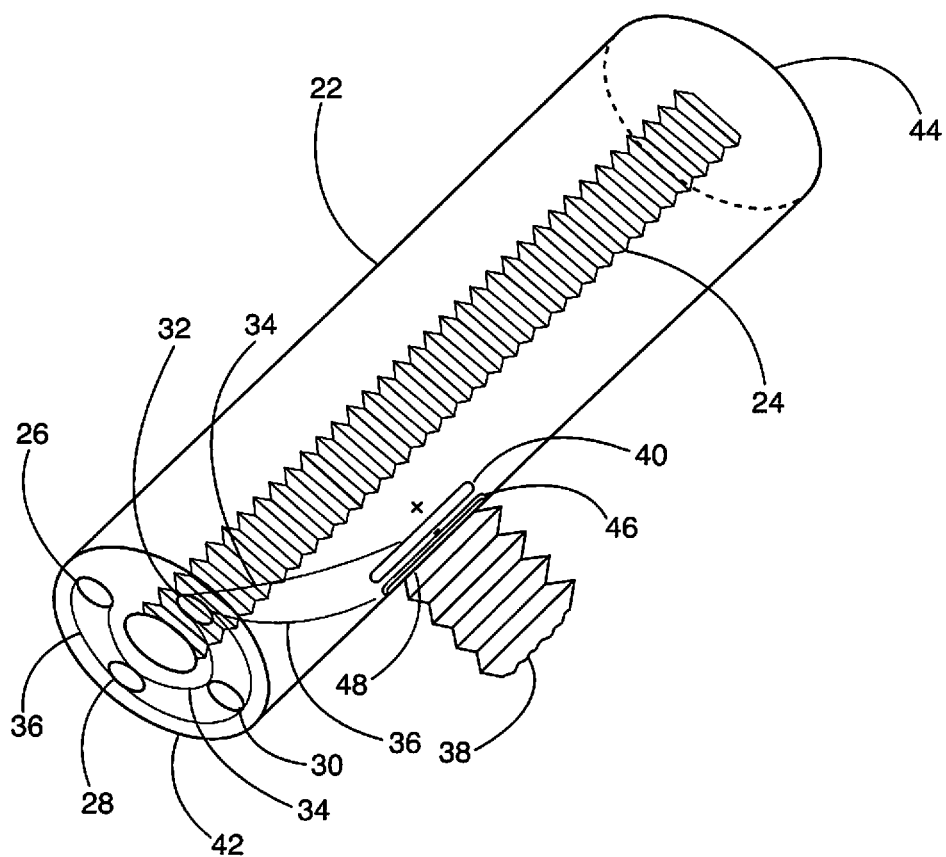
FIG. 2 is an enlarged sectional view of the light emitting diode (LED) cartridge containing a series of LED bulbs in accordance with the present invention.

FIG. 2 shows a side view of an LED cartridge 22 with an open front end 42 and an open rear end 44 and with a central axis comprising hollowed out tubing 24 that is lined with reverse threads so that LED cartridge 22 may be screwed on and attached to threads 18 of strut 16. The LED cartridge 22 consists of four separate tiny LED bulbs attached to open front end 42 of LED cartridge 22 and arranged circumferentially and peripherally at front end opening 42 and in a series starting with LED bulb 26 attaching to LED bulb 28 attaching to LED bulb 30 and finally attaching to LED bulb 32. A plurality of cathode wires 36 are connected to each LED bulb 26, 28, 30 and 32, wherein the cathode wire 36 of each LED bulb is attached to the cathode wire 36 of the next sequential LED bulb. A plurality of anode wires 34 are likewise connected to each LED bulb 26, 28, 30 and 32, wherein the anode wire 34 of each LED bulb is attached to the anode wire 34 of the next sequential LED bulb, thus forming a circuit, wherein anode wire 34 and cathode wire 36 extend from LED bulb 32 inside of LED cartridge 22 such that anode wire 34 attaches to anode side of coin shaped dry battery 40 and cathode wire 36 attaches to battery holder 46. LED bulbs are attached to the open end 42 of the attachable LED cartridge 22 with glue. Coin shaped dry battery 40 is held in place on its side by an electronically conductive metal battery holder 46 that is attached to inner side wall of LED cartridge 22. A thin piece of non-conductive material 38 is disposed between the cathode side of battery 40 and battery holder 46 to prevent electrical charge from passing through. The thin piece of non-conductive material connects to and hangs freely outside LED cartridge 22 through slit 48 in LED cartridge 22. Central axis of tubing 24 is shown having a diameter larger than any portion of the bayonet fitting 20 so that bayonet fitting 20 may slide through tubing 24. Tubing 24 is lined with reverse threads to complement the threads on strut 18 and is shown positioned in the center axis of the attachable LED cartridge 22 and not obstructing any of the material relationships defined above.

Figure 3:
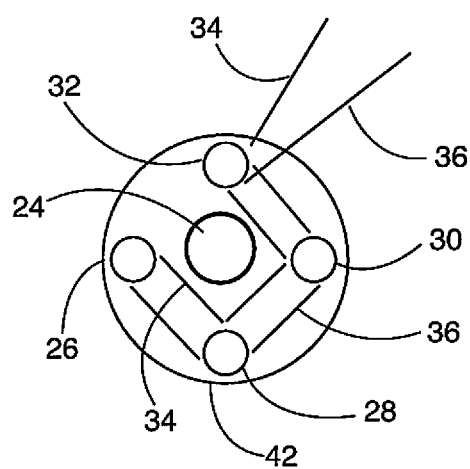
FIG. 3 is a cross-sectional view of the open front end of the light emitting diode (LED) cartridge containing a series of LED light bulbs and a central axis tubing in accordance with present invention.

FIG. 3 shows a cross sectional view of open front end 42 of LED cartridge 22 with four separate tiny LED bulbs 26, 28, 30, 32 arranged in a series circumferentially and attached peripherally to wall of LED cartridge 22 and starting with LED bulb 26 attaching to LED bulb 28 attaching to LED bulb 30 and finally attaching to LED bulb 32 and all connections to each other by means of cathode wire 36 connected to the cathode wire 36 of each subsequent LED bulbs and anode 34 wire connected to the anode wire 34 of each subsequent anode wire 34, forming a circuit wherein conducting wires anode 34 and cathode 36 extend from bulb 32 so that anode wire 34 attaches to anode side of dry coin shaped battery 40 and cathode wire 36 attaches to battery holder 46.

Figure 4:
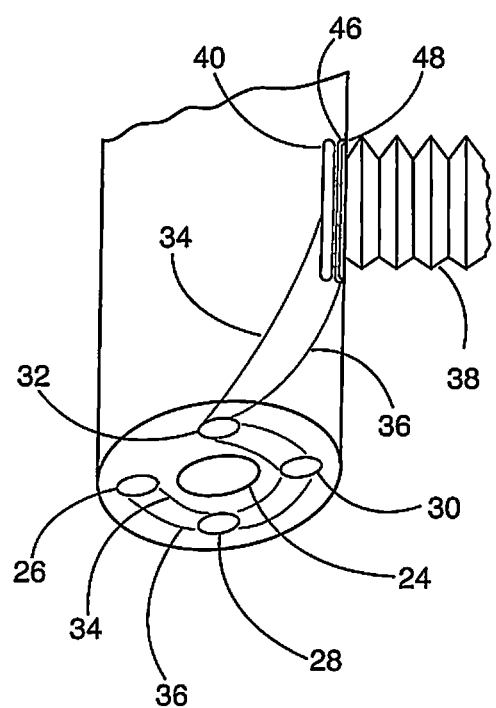
FIG. 4 is a perspective view of the attachable light emitting diode (LED) cartridge containing a battery holder, a dry battery, and a non-conductive material exposed to outside through a slit in cartridge in accordance with the present invention.

In FIG. 4 depicts an inside view of LED cartridge 22 with the conducting wire anode 34 attaching to the anode side of battery 40 and the conducting cathode wire 36 attaching to battery holder 46 made of electronically conductive metal to complete a circuit. A thin sheet of non-conductive material 38 is sandwiched between battery holder 46 and the cathode side of battery 40 to prevent contact from being made between cathode side of battery 40 and battery holder 46 and with material 38 having a portion of said material connecting to outside of LED cartridge 22 through slit 48.

Prior to surgery, the LED cartridge 22 is screwed onto barrel 10 by sliding the bayonet fitting 20 through central axis of tubing 24 of LED cartridge 22 and enabling LED cartridge 22 to be tightened on to strut support 16 of barrel 10 by twisting clockwise to matching threads. Finally, a surgical blade may then be attached to the bayonet fitting 20 as is done commonly in the art.

In its ordinary state without necessity of illuminating, the LED cartridge 22 provides that the anode wire 34 is always connected to the anode side of LED bulb 32 on one end and the anode side of battery 40 on the other end while cathode wire 36 is connected to the cathode side of LED bulb 32 on the one end and the battery holder 46 made of electrically conductive material on the other end. A thin sheet of non-conductive material 38 is disposed between battery holder 46 and anode side of battery 40 to prevent contact and illumination. When a surgeon wants to illuminate the surgical field while cutting, the surgeon can remove the non-conductive material 38 by gently sliding it free through the slit 48 and discarding said material enabling contact between cathode wire 36 attached to battery holder 46 and cathode side of battery 40 and completing a circuit to illuminate the surgical field.

After surgery is complete, if the surgical handle described herein is made of disposable material it may be disposed of in its entirety. If the surgical handle described herein is made of non-disposable material, than as is commonly done in the art, the blade will be removed from the bayonet fitting and then the LED cartridge 22 may be twisted off and disposed of while the remaining surgical scalpel handle may be properly sterilized prior to next use.

While this invention has been particularly shown and described in reference to the preferred embodiments thereof, it would be understood by those skilled in the art that various changes in form and detail may be made therein without departing from the scope and spirit of the invention encompassed by the impended claims. Although the embodiments have been described in reference to a scalpel handle with an illuminator, the present invention may also apply to any surgical instrument or device, or any medical device, that would require illumination immediately adjacent to and in advance of the device in order that said device may be used on or in the body for treating, excising, incising or diagnosing including but not limited to surgical laser instruments, endoscopes, curettes, surgical wire instruments, scalpels, and other surgical instruments. Numerous modifications, changes, variations, substitution and equivalents will be apparent to those skilled in the art without departing from the spirit and scope of the invention as described in the claims.

REFERENCES

U.S. Pat. No. 6,483,651, U.S. Pat. No. 6,733,150, U.S. Pat. No. 6,999,248 B2 and U.S. Pat. No. 7,566,139.

What is claimed as new and desired to be protected by Letters Patent of the United States is:

1. A surgical scalpel with an attachable illuminator comprising:
   an elongated handle having a front end and a solid rear end, the front end having a front end aperture;
   a support strut aligned with a central axis of the handle and passing through the front end aperture of the handle, the support strut tapering at a distal end into a bayonet fitting for attaching a blade to the handle; and
   a removable light emitting diode cartridge defining the illuminator and having an open front end with a series of light emitting diode bulbs, an open rear end, and a battery, wherein the cartridge is inserted onto the front end of the handle and coaxial with the central axis.

2. The surgical scalpel of claim 1, wherein the series of light emitting diode bulbs comprises a plurality of light emitting diode bulbs connected sequentially by cathode conducting wires and anode conducting wires.

3. The surgical scalpel of claim 2, wherein the cathode conducting wires are attached to a cathode of the battery and the anode conducting wires are connected to an anode of the battery.

4. The surgical scalpel of claim 3, wherein a non-conductive material is removably disposed between the anode conducting wires and the battery.

5. The surgical scalpel of claim 4, wherein removal of the non-conductive material allows an electrical circuit to be completed between the cathode conducting wires, the anode conducting wires and the battery, wherein upon completion of the electrical circuit the light emitting diode bulbs may be illuminated.

6. The surgical scalpel of claim 3, wherein a non-conductive material is removably disposed between the cathode conducting wires and the battery.

7. The surgical scalpel of claim 6, wherein removal of the non-conductive material allows an electrical circuit to be completed between the cathode conducting wires, the anode conducting wires and the battery, wherein upon completion of the electrical circuit the light emitting diode bulbs may be illuminated.

8. The surgical scalpel of claim 2, wherein the series of light emitting diode bulbs comprises four light emitting diode bulbs.

9. The surgical scalpel of claim 1, wherein the surgical scalpel is disposable.

10. The surgical scalpel of claim 1, wherein the illuminator is disposable.

11. The surgical scalpel of claim 1, wherein the front end is hollow, wherein further the cartridge is inserted into the front end of the handle by passing the support strut through the open rear and front ends of the cartridge, and wherein the cartridge is attached to the support strut via threads.

12. A method of illuminating a surgical field immediately adjacent to and in advance of a surgical scalpel blade, comprising use in surgery of a surgical scalpel having an attachable illuminator, wherein the illuminator is activated to provide illumination to the surgical field, wherein the surgical scalpel comprises:

an elongated handle having a front end and a solid rear end, the front end having a front end aperture;
a support strut aligned with a central axis of the handle and passing through the front end aperture of the handle, the support strut tapering at a distal end into a bayonet fitting for attaching a blade to the handle; and
a removable light emitting diode cartridge defining the illuminator and having an open front end with a series of light emitting diode bulbs, an open rear end, and a battery, wherein the cartridge is inserted onto the front end of the handle and coaxial with the central axis.

13. The method of claim 12, wherein the series of light emitting diode bulbs comprises a plurality of light emitting diode bulbs connected sequentially by cathode conducting wires and anode conducting wires.

14. The method of claim 13, wherein the cathode conducting wires are attached to a cathode of the battery and the anode conducting wires are connected to an anode of the battery.

15. The method of claim 14, wherein a non-conductive material is removably disposed between the anode conducting wires and the battery.

16. The method of claim 15, further comprising removal of the non-conductive material and thereafter completion of an electrical circuit between the cathode conducting wires, the anode conducting wires and the battery, wherein upon completion of the electrical circuit the light emitting diode bulbs are illuminated.

17. The method of claim 14, wherein a non-conductive material is removably disposed between the cathode conducting wires and the battery.

18. The method of claim 17, further comprising removal of the non-conductive material and thereafter completion of an electrical circuit between the cathode conducting wires, the anode conducting wires and the battery, wherein upon completion of the electrical circuit the light emitting diode bulbs are illuminated.

19. The method of claim 13, wherein the series of light emitting diode bulbs comprises four light emitting diode bulbs.

20. The method of claim 12 wherein the surgical scalpel is disposable.

21. The method of claim 12, wherein the illuminator is disposable.

* * * * *